(12) United States Patent
Regimand et al.

(10) Patent No.: US 8,020,451 B2
(45) Date of Patent: Sep. 20, 2011

(54) SYSTEM AND METHOD FOR CONDITIONING AND DETECTION OF MOISTURE DAMAGE IN ASPHALT MIXES

(75) Inventors: Ali Regimand, Raleigh, NC (US);
Lawrence H. James, Raleigh, NC (US);
Peter D. Muse, Durham, NC (US);
Keith Landreth, Raleigh, NC (US);
Tianqing He, Cary, NC (US)

(73) Assignee: InstroTek, Inc., Raleigh, NC (US)

( * ) Notice: Subject to any disclaimer, the term of this patent is extended or adjusted under 35 U.S.C. 154(b) by 442 days.

(21) Appl. No.: 12/217,778

(22) Filed: Jul. 9, 2008

(65) Prior Publication Data

US 2010/0005898 A1    Jan. 14, 2010

(51) Int. Cl.
*G01N 3/12* (2006.01)
*G01N 15/08* (2006.01)
*G01N 9/14* (2006.01)

(52) U.S. Cl. .................................. 73/803; 73/38; 73/437
(58) Field of Classification Search .................... 73/803, 73/38, 437
See application file for complete search history.

(56) References Cited

U.S. PATENT DOCUMENTS

| | | | | |
|---|---|---|---|---|
| 2,539,355 A * | 1/1951 | Reichertz | ........................... | 73/38 |
| 4,487,056 A * | 12/1984 | Wiley | ............................... | 73/38 |
| 5,365,793 A * | 11/1994 | Terrel et al. | ..................... | 73/813 |
| 5,987,961 A | 11/1999 | Harris et al. | ................. | 73/11.01 |
| 6,321,589 B1 * | 11/2001 | Regimand | ..................... | 73/32 R |
| 6,526,836 B1 | 3/2003 | Brouse | ............................. | 73/818 |
| 6,615,643 B2 | 9/2003 | James et al. | ........................ | 73/73 |
| 6,684,684 B2 * | 2/2004 | Regimand et al. | ................. | 73/38 |
| 6,799,471 B1 | 10/2004 | Regimand et al. | .............. | 73/803 |
| 6,817,230 B2 * | 11/2004 | James et al. | ....................... | 73/73 |

OTHER PUBLICATIONS

Testing for Debonding Asphalt from Aggregates, R.A. Jimenez Transportation Research Record (1974).
Development and Evaluation of Test Methods to Evaluate Water Damage and Effectiveness of Antistripping Agents, Birgisson et al, Final Report Florida Dept. of Transportation (2005). A Test Method for Identifying Moisture Susceptible Asphalt Concrete Mixes, Alam et al, Center for Highway Materials Research, University of Texas at El Paso (1998).
ASTM Designation D4867/D4867M-96 "Standard Test Method for Effect of Moisture on Asphalt Concrete Paving Mixtures" pp. 481-484 (1996).
AASHTO Designation T283-89 "Resistance of Compacted Bituminous Mixture to Moisture Induced Damage" pp. 1040-1043 (1989).

* cited by examiner

*Primary Examiner* — Lisa Caputo
*Assistant Examiner* — Punam Roy
(74) *Attorney, Agent, or Firm* — Myers Bigel Sibley & Sajovec

(57) ABSTRACT

An apparatus and method for determination of susceptibility of asphalt concrete materials to moisture damage. An asphalt sample of known bulk specific gravity (density) is placed inside a chamber filled with water, which is capable of heating the sample to a pre-determined temperature. The chamber is pressurized by introduction of air pressure to a flexible membrane that decreases the volume within a chamber containing the sample and water, increasing the pore pressure in the sample. The pressure is then released and allowed to come to ambient pressure. This process is repeated a predetermined number of times (cycles). When a selected number of cycles are complete, the asphalt sample is removed from the chamber and its bulk specific gravity (density) measured again. The difference between the density before and after conditioning is an excellent method of rating the degree at which moisture would deteriorate asphalt samples due to introduction of moisture. The cyclic nature of the increased/decreased pore pressure is observed to significantly decrease bulk specific gravity (density) for poor quality asphalt designs. Furthermore, the sample conditioned by this method can be used for other conventional mechanical test methods, such as tensile strength and modulus determination. Computerized controls are used to automate the procedure and to record and display data from sensors.

18 Claims, 3 Drawing Sheets

SYSTEM AND METHOD FOR CONDITIONING AND DETECTION OF MOISTURE DAMAGE IN ASPHALT MIXES

FIELD OF THE INVENTION

This invention relates generally to equipment and method for testing pavement mixes, commonly called asphalt, for the potential for water damage. More specifically, this relates to using water in a chamber that is cyclically pressurized to simulate the action of water being pressed into and pulled out of the wet pavement by tires on a roadway. The cyclic pressure in the chamber containing the asphalt sample will cause loosening of the bond between individual aggregate particles for moisture susceptible mixtures and would significantly reduce the measured density of the sample. Reduction in density is a good indicator of moisture susceptibility of a mixture.

BACKGROUND OF THE INVENTION

Paving mixes known as asphalt consist of approximately 95 percent aggregates and five percent liquid binder. The mixture should be designed to create the best possible bond between the liquid binder and the aggregate. Moisture can penetrate asphalt, which causes an adhesive failure between the binder and the aggregate or water can soften or emulsify the binder film. In either case, water can reduce the strength of the mixture of the asphalt. When the liquid binder is stripped from the asphalt, the aggregate can become scattered (called raveling) or lost. Loss of strength in mixtures can result in pot holes in the pavement or cracking or raveling or rutting.

It is well understood that moisture can strip the binder from the aggregates, resulting in a form of failure called "stripping" of an asphalt pavement. The cause of moisture damage to asphalt is multifactorial. First, the type of aggregates used in the mixture affect the susceptibility of the mixture with the binder to moisture damage. For example, residual clay left in aggregates after washing can cause a serious problem. Clay expands when it absorbs the water and creates a barrier between the aggregates and the binder effectively reducing the adhesion or cohesion of the bond between the binder and the aggregates. The composition of the binder also plays an important role in the resistance of the asphalt to moisture damage. The binder viscosity is affected by the mixing temperature in the plant and the ingredients of the binder, such as polymers and rubbers, can also affect the ability of the binder to coat the aggregate surface and to keep the aggregates bound. The binder emulsification has to be controlled to give strength and resistance to moisture for the asphalt. The aggregates should be dried carefully at the plant. Typically, there should be no more than 0.5% moisture retained in the plant produced mix. If water remains in the aggregates, then, during the actual laying of the pavement, steam can be produced which causes stripping of the binder from the aggregate. Controlling the amount of field compaction is necessary to reduce the amount of external water that can penetrate the pavement. A compact pavement with the optimum density and lack of air voids will reduce water permeability, hence reduce the possibility of water damage. However, compaction can be carried too far, which can cause rutting due to mixture instability. If, during construction, there are layers of asphalt mixtures, water can be trapped between the pavement layers. Segregation which is caused by aggregates gradation change when laying down the pavement can have a detrimental affect on asphalt pavement and induce moisture damage. Proper drainage is critical in design and construction of asphalt pavement. In many of these failure modes, the density of the compacted material is reduced. For example, as bond strength between individual aggregate particles is reduced, the mixture will tend to lose strength and additional air channels are created within the compacted mixture, which correlates to the drop in density.

It is apparent, from the above discussion, that susceptibility to water damage or stripping to an asphalt pavement can arise from many sources. Even an ideal mixture of binder and aggregate properly processed or installed can still be susceptible to water damage. Evaluation of moisture susceptibility has become an important part of volumetric design procedure and pavement construction quality control. However, the most important test to determine the susceptibility of water damage for an asphalt mixture requires testing the compacted asphalt mixture in a way that will predict susceptibility of that compacted mixture to water damage.

In our previous U.S. Pat. No. 6,799,471, a two tank system was used to apply moisture damage to the asphalt concrete specimens. This device required a source of high flow pressurized air. As one tank is opened to the air, the other would be pressurized and maintain pressure while forcing water to the other tank through a restricted valve. Once the water reached a certain level, the pressurized tank would open and the open tank would be pressurized forcing the water back the other way. A drawback to this device was that it required a large amount of valving and a pump to keep the water circulating. Another drawback was this device was bulky for field laboratories and its repeatability was highly dependent on the air supply available at each lab. The most widely used test for moisture sensitivity is covered under American Association of State Highway and Transportation Official (AASHTO) specification T283 and American Society of Testing and Materials (ASTM) D4867. In both of these methods 2 sets of samples of asphalt of approximately 6 inch in diameter by 4 inch thickness are compacted to 7% air voids in laboratory compaction equipment. Air voids is determined by the ratio of the compacted sample density to the maximum density of the mixture. The compacted sample density and maximum density of the mixture can be determined based on standard test methods used in asphalt laboratories. The mixture can be prepared in the laboratory or can be obtained from a field site. One set is saturated with water and is kept in a temperature controlled water bath at 60 degree C. for 17 to 24 hours. The control set is kept at room temperature (25 degree C.). In some situations (cold climates), the sample set is also kept at degree C. for extended time to provide a climatic cycle of cold to hot. Both conditioned (sample) and unconditioned (control) sets are then placed in a break press and broken to determine the pressure at which the sets break apart. The ratio of unconditioned (control) to conditioned (sample) sets break pressure is then used to determine the sensitivity of the mixture to moisture damage. If this ratio (Conditioned sample strength/Unconditioned sample strength) is over 70, then the mixture passes this test and is deemed acceptable. A visual inspection of the broken conditioned sample may reveal adhesion loss and provide useful information in the inspection stage. The acceptance ratio varies and can range from 70 to 85 depending on the agency and the mixture type. Unfortunately, the reliability and repeatability of this test is very poor, the test does not simulate the true dynamics of the field conditions and the results cannot be correlated to the actual field performance. Furthermore, this test does not effect any change in the density of the sample and the only effect caused by this test could be at the molecular level.

In an attempt to create pore pressure within a compacted sample and to better emulate the actual field conditions, in 1974, Rudy Jimenez of Arizona introduced the Double Punch method. This method included a compacted sample that was held under load by a punch or a plate from top to bottom of the sample. The sample was kept under water and a sinusoidal load (5-30 psi) was applied to the sample repeatedly. Even though this method could introduce pore pressure within the sample, it still did not simulate the actual dynamics of the water movement in and out of the pavement through tire activity. Furthermore, the testing time is too long with sophisticated equipment and does not correlate to field performance.

Recently, wheel rutting devices have been used to predict stripping and moisture damage. These devices use a small wheel that travels back and forth on a compacted sample that is immersed in 50° C. water. Force is applied to the wheel in various amounts. Although these devices can predict the rutting rate in the pavement, the results have not been correlated to stripping or moisture damage.

Another system that has been used in research is called an Environmental Conditioning Chamber (ECS). This device was developed at Oregon State University in 1987. In this test, a sample is placed in a chamber filled with 60° C. water and confining pressure of 2.5 in Hg. A conditioning direct load of 200 lbs. is applied on the sample for 0.1 sec. and then released for 0.09 sec. In this device the resilient modulus of the sample is measured before and after the loading/conditioning process. Empirical criteria is developed based on performance of known mixes to establish pass/fail limits for moisture damage. Unfortunately, this test takes 6-18 hours and so far has had poor repeatability. Also, the apparatus needed to conduct this test is extremely expensive and large for a typical laboratory application in the construction industry. This apparatus is mainly used for research and is not widely available.

Harris et al., U.S. Pat. No. 5,987,961, discloses an apparatus for testing asphalt. Rollers are driven over a pair of pavement samples placed in trays beneath the wheels. The samples are placed in trays which are in a water bath. It is controlled by a computer which continuously monitors where the pavement sample is by a displacement transducer. Terrell et al., U.S. Pat. No. 5,365,793, discloses an asphalt sample in a sealed container. A pressure differential is created across the asphalt and passes water or air or a mix through the asphalt sample by the differential pressure between the vacuum and the supply of fluid which flows through the specimen. For the Terrell device, a typical test procedure will take more than twelve hours.

A study was conducted by University of Florida in June of 2005, titled "Development and Evaluation of Test Methods to Evaluate Water Damage and Effectiveness of Anti-Stripping Agents". This method consists of a moisture saturated sample confined in a rubber membrane submerged in water under a fixed pressure. A cyclic physical load is then applied to the sample by means of plates attached to a piston, while water surrounding the sample remains under constant pressure and temperature. This device applies a physical pressure (squeeze) to the sample. The cyclic squeezing action of the sample creates a pore pressure within the sample. The physical load on the sample in the Florida study only effects small pore volume changes in the sample and depends significantly on the type and characteristics of the mixture. This device requires a significant amount of floor space and is too expensive for normal asphalt laboratories.

Despite this earlier work it would be an advance in the art to provide an instrument and testing method that can be used during design and quality control to determine the stripping potential and moisture susceptibility of an asphalt mix. The device should use pressure cycles in which water is forced in and then drawn out of the pores in asphalt. The device should be simple to operate, small so that it would fit inside normal field construction labs and provide an evaluation method, such as density difference, that is practical and can be tested before, during and after the construction of asphalt pavements. All asphalt laboratories are equipped with instruments for measurement of bulk density. Bulk density tests are performed with standard test methods readily available in the industry and one can produce results in less than five minutes. Sample density can be measured before and after moisture sensitivity test and any decrease in density can be directly correlated to the sensitivity and quality of the asphalt mixture. The testing time should be relatively short in time. It should produce repeatable results and should be capable of testing field and laboratory fabricated samples of any size.

SUMMARY OF THE INVENTION

The current invention subjects an asphalt sample to the wear behavior of wet road paving materials subjected to the stresses from the tire loads produced by vehicular traffic. When a tire rolls on a wet asphalt surface the material is subject to three phases of stresses, an initial pressure phase where tire initially makes contact with the surface and the water is forced into the pores of the asphalt creating large pore pressures, a relaxation phase where the tire is in contact with the road for a period of time and the water begins to disperse beneath the tire, and a reverse pressure phase where the surface of the tire leaves the surface of the asphalt road. The current invention is used to evaluate the quality of asphalt design by speeding up the process using an elevated temperature and repetitively applying and releasing pressure in order to subject the sample to the action of a tire on an asphalt pavement surface. Poor asphalt will reflect this by showing a decrease in bulk specific gravity (density) of the sample when comparing the density from before to after the test. In a moisture susceptible pavement, pore pressure weakens the bond between the individual rocks, which causes loosening of the bond between individual aggregate particles and is correlated to a drop in the density and eventual cause for raveling of rocks, moisture damage to the roadway and pot holes.

DETAILED DESCRIPTION OF THE DRAWINGS

Figure 1:
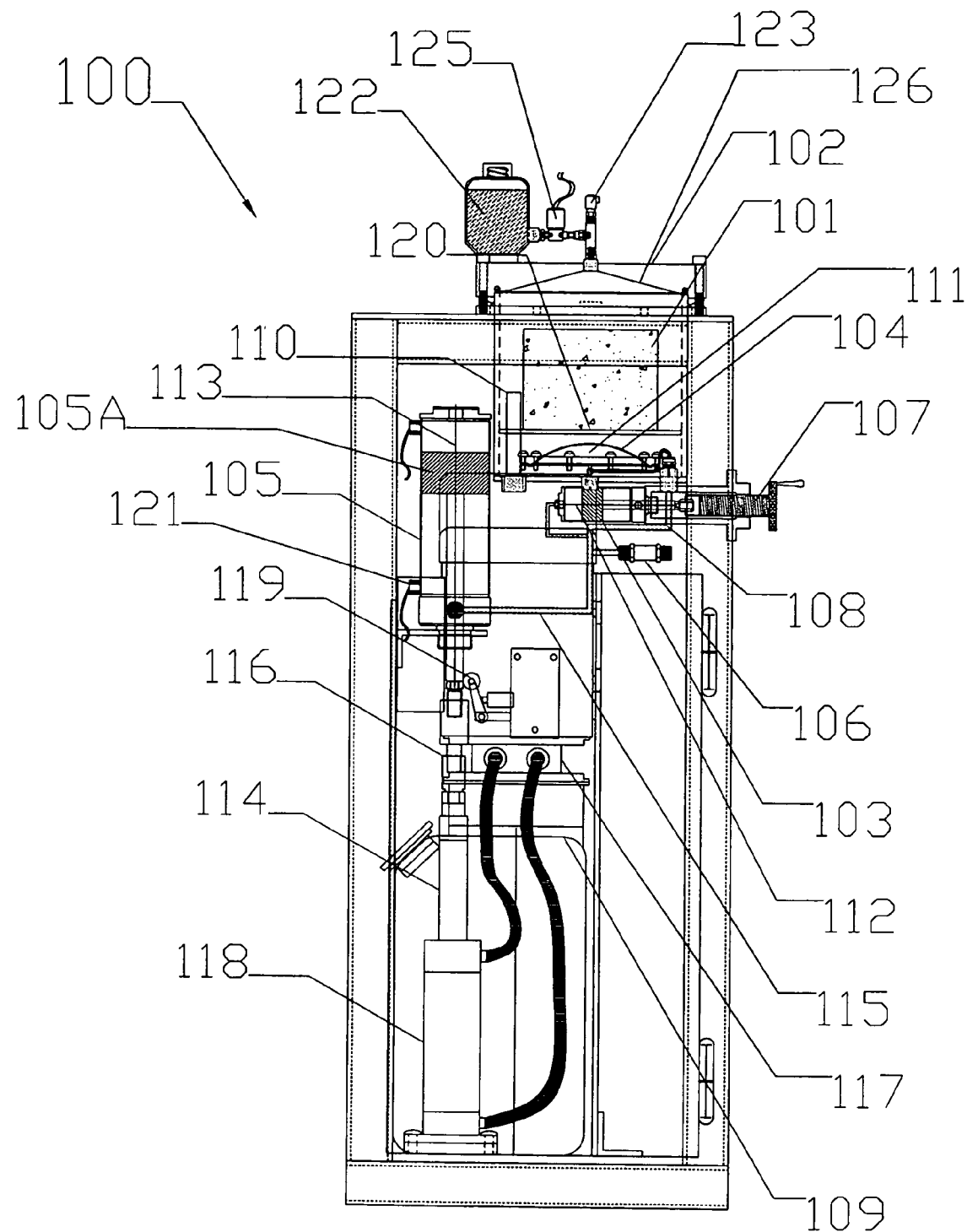
FIG. 1 shows one embodiment of the invention demonstrating the operation of the pressure application process.

FIG. 1 shows the preferred embodiment of the moisture damage inducing device (100). Sample (101) of known density is placed into a sealable tank (102) filled with water and rests on internal support (120). The density can be measured by water displacement method or other methods routinely employed for determination of sample density. Standard methods for measurement of density are specified under ASTM test methods D2726 and D6752. Before placing the conical lid (126) on the tank (102) and sealing the tank (102) residual air has to be removed from the tank (102). If too much air is left in the tank (102), it will be difficult to achieve high pressures inside the tank (102). If residual air exists in the pores of the sample (101), the air may become dislodged and rise in the tank (102). This air may be bled from the system by using the conical shape on the inside surface of the conical lid (126). The conical lid (126) will allow the air to move to the tip of the cone, where a bleed valve (123) is placed. The bleed valve (123) can be controlled electronically by using an ASCO valve (Florham Park, N.J.), which can be opened and closed through computer commands. Additionally, a water reservoir (122) is used to fill the tank (102) to its capacity, once any residual air is removed from the tank (102). The reservoir (122) can also be controlled by using electronic water valve (125) and computer controls. In operation, the moisture damage inducing device (100) is allowed to run at high pressure for a few cycles. The moisture damage inducing device (100) is then stopped and the bleed valve (123) is opened to let residual air out and then closed. The water reservoir valve (125) is opened and the tank (102) is filled to capacity. The reservoir (122) is placed above the sealable tank (102) and will automatically replenish the water in the sealable tank (102) by the amount of air space available. This process is repeated multiple times before the start of the test to make sure all residual air is removed from the sealable tank (102). The entire process is controlled through software. Obviously, this air bleeding process can also be accomplished manually by opening a hand operated bleed valve after a few cycles, letting air out and using a syringe or other water containers to back fill the tank with water. Once the air bleeding process is complete, heater (110) will continue raising the water temperature to the desired level. Once the set temperature is reached, active air cylinder (105) with sensors (121) to detect piston position, moves up reducing the total connected volume (112) of passive air cylinder (103), volume (113) of the active cylinder (105), and volume (113) of the expandable membrane (104). Pressure increases as the volume (113) of active cylinder (105) is reduced. Water in tank (102) is separated from air in the expandable membrane (104). The expandable membrane (104), in intimate contact with the water in the tank (102), transmits the pressure to the water in tank (102) thereby applying pressure to pores in sample (101).

An adjustment mechanism (107) is to be used to adjust the pressure sealable tank (102). The adjustment mechanism (107) increases or decreases the volume (112) of the passive air cylinder (103). The volumes of the passive air cylinder (103), the inflatable bladder (104), and the active air cylinder (105) are connected. By decreasing the volume (112) of the passive air cylinder (103) enables more air to be forced into the expandable membrane (104) as the volume (113) of the active air cylinder (105) is decreased. In the active air cylinder (105), a piston (105A) is driven by the hydraulic piston (118). As hydraulic fluid is forced into one end of piston (118) connected to hydraulic piston shaft (114) the hydraulic piston shaft (114) forces the piston (105A) upward causing the volume (113) in the active cylinder (105) to decrease. Switch (119) is activated. Hydraulic fluid from reservoir (109) is forced into the other end of the hydraulic piston (118) reversing the direction of the piston and increasing the volume (113). A motor (115) turns the pump (117), forcing hydraulic fluid from a reservoir (109) into the hydraulic piston (118). As hydraulic fluid is forced into one end of piston (118) connected to hydraulic piston shaft (114), the hydraulic piston shaft (114) forces the piston (118) upward causing the volume (113) in the active cylinder (105) to decrease. When switch (119) is activated, hydraulic fluid from the reservoir (109) is forced into the other end of the hydraulic piston (118) reversing the direction of the piston (118) movement and increasing the volume (113). As the volume of (113) decreases, volume of air in the expandable membrane (104) increases, forcing water in the sealable tank (102) into the sample (101). Maximum pressure is obtained when the volume (113) of the active cylinder (105) is transferred to the volume (111) of the inflatable bladder (104) and the volume (112) of the passive air cylinder (103) is at a minimum by using the adjusting mechanism (107). When the active piston (105A) is at the bottom of a downstroke, a control (121) opens valve (106) to allow air in the passive air cylinder (103), the expandable membrane (104), and the residual volume (111) to equalize with atmospheric air. This assures that at the beginning of the upstroke of the piston (105) the air pressure is ambient air pressure in the active cylinder (105), the passive cylinder (103), and the expandable membrane (104). It can be readily seen that the active piston (105A) can be driven up and down by the hydraulic piston (118). Motion of the piston (118) can continue in a cycling fashion alternately applying pressure to the sample (101) and relieving the pressure applied to the sample (101). Those skilled in the art will recognize other means of applying pressure using other kinds of actuating mechanisms. Hydraulic, pneumatic, linear motor, or rotary motors are examples not shown which will also serve the purpose of driving the active piston (105A) to apply pressure in the sample. At the end of a predetermined number of cycles, the sample is removed and its density measured by standard testing methods such as ASTM D2726 or ASTM D6752. Decrease of more than 0.5% in density from before to after the cyclic moisture sensitivity test has shown a strong correlation to weak moisture performance mixtures on the roadway. Unlike methods such as the double punch method or the wheel rutting method, no physical force is applied to the asphalt mix. Physical contact from a wheel or a punch tends to compact the mixture increasing its density and make it impossible to determine the susceptibility to water damage by density testing.

Figure 2:
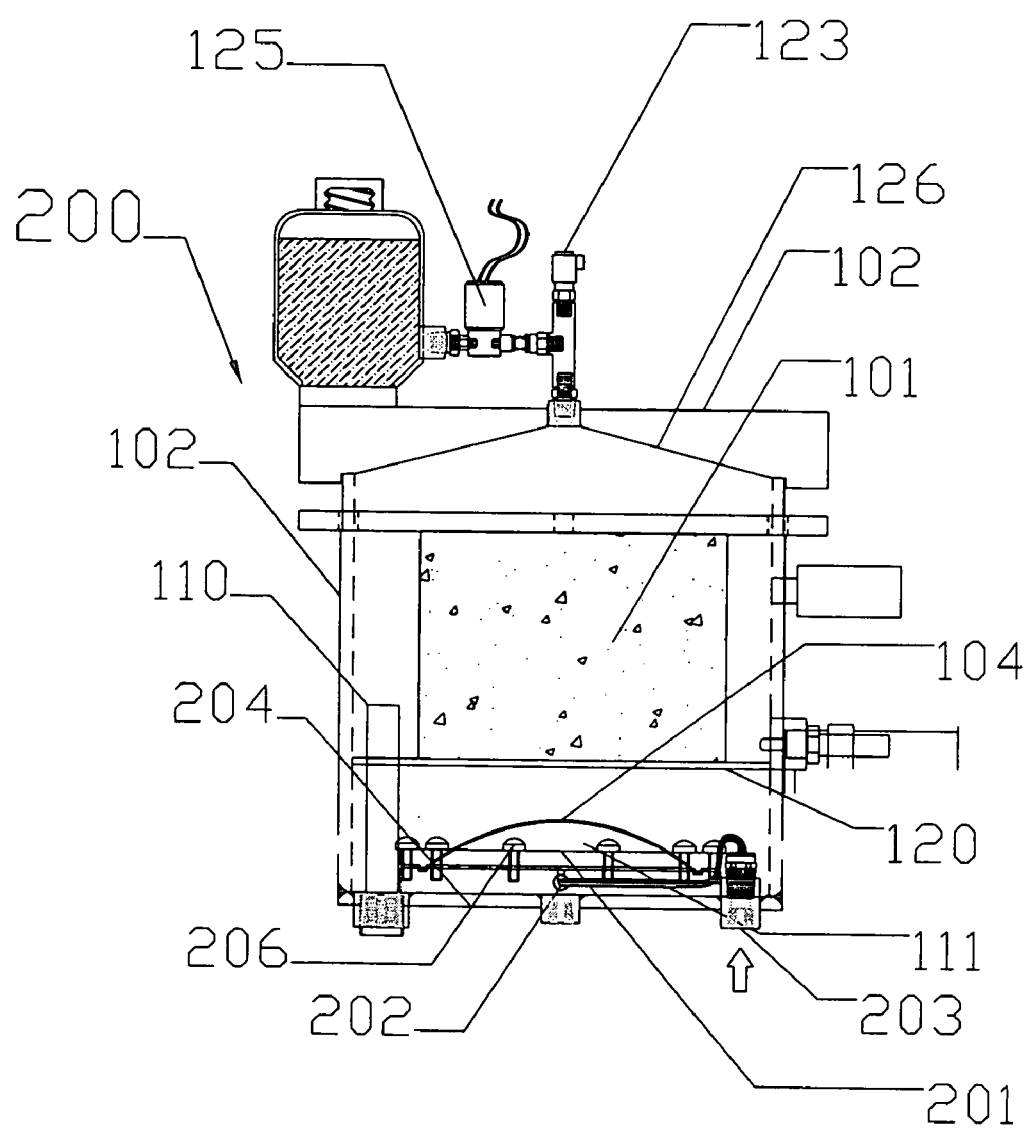
FIG. 2 shows a detailed view of the sample container and a diaphragm used to transfer the pressure to the water.

FIG. 2 shows a detailed view preferred embodiment of sealable tank (102). Flexible membrane (104), flexible membrane ring guard (201), and flexible membrane support (202) show the mechanism for transferring externally applied pressure to the internal volume of sealable tank (102) and to sample (101) of sealable tank (102). Flexible membrane (104) is fastened to flexible membrane support (202) which rests on tank bottom (204). Flexible membrane (104) has a diameter such that ring guard (201) rests completely on flexible membrane (104) securely to flexible membrane support (202). Flexible membrane ring guard (201) is secured to flexible membrane support (202) by fasteners (206). Flexible membrane (104) is made of a flexible and expandable material so that as pressure increases in volume (111), it expands to account for small residual air not completely removed from inside sealable tank (102) and inside sample (101) but is prevented from further expansion by the incompressibility of water. Those skilled in the art will recognize that there are other ways to accomplish the result of flexible membrane (104), flexible membrane support base (202), and flexible membrane ring guard (201). These include but are not limited to applying the flexible ring guard (201) directly to sealable tank bottom (204) to restrain flexible membrane (104), replacing flexible membrane (104), flexible membrane support base (202), and flexible membrane ring guard (201) with a single rubber bladder.

A critical element of sealable tank (102) is the design of the conical lid (126) in order to reach a desired pressure setting and application of consistent pressure from one cycle to the next. It is important that air trapped inside the sealable tank (102) be removed. The underside of conical lid (126) has an upward slope toward the center of the conical lid (126). Any residual air inside sealable tank (102) will move up and because of the slope on conical lid (126) will subsequently move to the center of conical lid (207) where it can be removed by bleed valve (123) thereby assuring maximum and consistent pressure is achieved.

Figure 3:
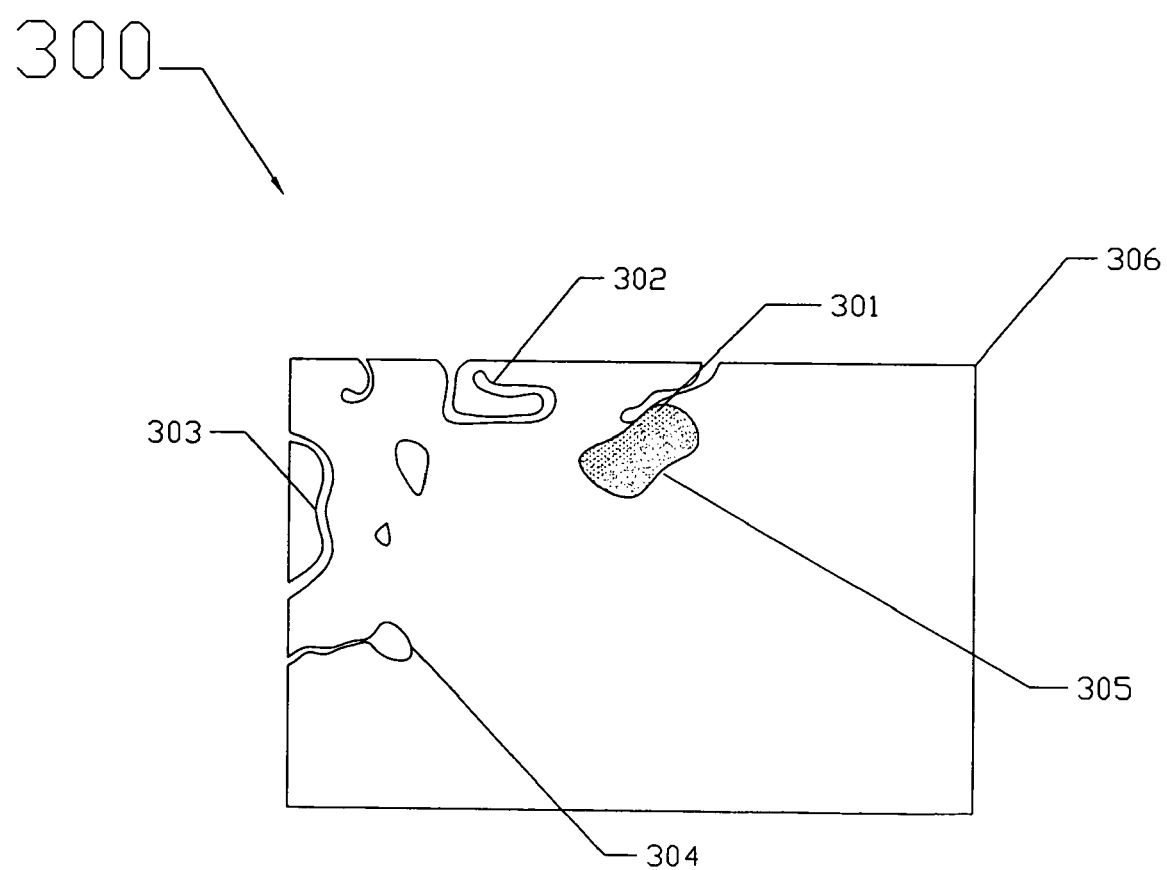
FIG. 3 shows several different void structures in an Asphalt concrete sample.

FIG. 3 depicts an asphalt core. As mentioned above moisture damage to asphalt is multifactorial, however FIG. 3 depicts a sample (300) with different void structures. Void (301) shows a void lying next to aggregate (305). Void (304) represents a void that may be semi-connected and does not fully saturate until pressure is applied. Void (303) is an interconnected void that makes its way from the surface and meanders back to the same surface. All these voids will react differently to applied pressure, void (301) may cause the binder to separate from the aggregate allow water to infiltrate into the voids themselves. As mentioned above if clay is present an expansion may take place. A void such as (304) may allow an agitating motion of the water as pressure is applied and removed resulting in an emulsifying condition and expanding the pore size. As repetitive cyclic pressure is applied, bond between individual aggregate will weaken and break. The loosening and break in bond between aggregates will create additional voids, crack and air channels with compacted mixtures. The additional air volume within the mixture will decrease the density of the cpmpacted mixture. Mixtures with strong bond will suffer very little change in density. However, density of poor and moisture susceptible mixture will reduce significantly. The apparatus and method of this invention will provide an easy, inexpensive, and practical method for measurement of moisture susceptibility in the laboratories. The conditioning method is automatic with little operator involvement and the density measurement change proposed for determination of moisture sensitivity is simple and can be performed with existing equipment already available in almost all asphalt laboratories.

Theory and Data:

The action of the device can be understood from the ideal gas law, more specifically Boyle's Law. Where given an initial volume Vi, an initial pressure pi, a final pressure Pf, and a final volume V f the relationship between these variables is given below.

$$P_i V_i = p_f V_f$$

In the case cited above we must identify the volumes before any quantitative analysis may be accomplished. For the initial volume Vi we have the following:
Via=initial volume (113) of the active cylinder (105),
Vip=initial volume (112) of the passive cylinder (103),
Vir=initial unknown residual volume in tank (102),
Vis=initial unknown residual volume in sample (101),
Vib=initial volume (111) of flexible membrane (104).
For the final volume Vf we have the following:
Vfa=final volume (113) of the active cylinder (105),
V fp=final volume (112) of the passive cylinder (103),
Vfr=final unknown residual volume in tank (102),
V fs=final unknown residual volume in sample (101),
V fb=final volume (111) of flexible membrane (104).

The quantities we know are V fa which we will take to be zero, and V fp which is equal to Vip and will simply be denoted as V p, and Vib which we take to be zero. Our equation becomes:

$$p_i(V_{ia}+V_p+V_{ir}+V_{is}) = p_f(V_p+V_{fr}+V_{fs}+V_{fb})$$

From this we see that the final pressure we are able to obtain is determined by residual tank volume Vir, the volume Vis of the sample volume. If we are able to saturate the sample completely and remove all residual air the equation simplifies to the one below.

$$p_i(V_{ia}+V_p) = p_f(V_p)$$

Note that volume (111) of flexible membrane (104) does not appear since water is incompressible and there are no compressible air voids. Looking at equation above it is simple to observe that if the initial volume (113) of the active cylinder (105) is equal to volume (112) of passive cylinder (103) then the absolute pressure increases to twice the original value. If sample (101) is fully saturated then it experiences that pressure against it's internal structure which was manufactured at normal atmospheric pressures.

The current method, American Association of State Highway and Transportation Official (AASHTO) specification T283, moisture sensitivity is to measure the tensile strength at which a conditioned sample breaks compared to an unconditioned sample and do a visual inspection to identify the degree of stripping. Results from testing samples conditioned using the current invention to apply cyclic pressure loads under heated conditions indicate that poor asphalt samples which are susceptible to moisture damage and stripping suffer a reduction in bulk specific gravity (density) compared to the original bulk specific gravity (density). A reduction of 0.5% in bulk specific gravity (density) has shown good correlation to roadway mixtures that are weak and susceptible to moisture damage. Data from several different materials tested is shown in the table below.

| Sample Number | Condition Pressure (psi) | Density Before Condition (g/cm3) | Density after Condition (g/cm3) | % Diff | Pass/fail Criteria |
|---|---|---|---|---|---|
| 1 | 42 | 2.250 | 2.173 | 3.4 | Fail Marginal Mix |
| 2 | 42 | 2.251 | 2.206 | −2.0 | Fail Marginal Mix |
| 3 | 45 | 2.469 | 2.471 | +0.08 | Good mix |
| 4 | 45 | 2.468 | 2.471 | −0.12 | Good mix |

Data Using the Apparatus of the invention Cycles 10,000, Temperature 60 C

The samples tested in the table above are mixes used in North Carolina. The apparatus and method disclosed in this invention was used for testing the above samples. The accepted test method in North Carolina for moisture susceptibility of mixtures is AASHTO T283. This test examines the tensile strength ratio (FSR) of samples that have been conditioned at 60° C. for 24 hours versus samples that have not been conditioned. This test indicated TSR of above 90% for materials used in sample 1 and 2. TSR of 80% and higher are deemed acceptable under the requirements of most states. However, this mixture failed after 3 weeks in service due to moisture damage. The results obtained from the current invention (above table) showed a significant drop in density for samples of moisture susceptible mixtures conditioned by this invention. Using the results obtained from the method of this invention would have prevented these mixtures from being applied in the field and would have saved millions of dollars in removal and replacement of these mixtures.

We claim:

1. An apparatus to treat an asphalt sample for detection of susceptibility to moisture damage for asphalt mixes comprising:
   (a) at least one chamber, the chamber openable and closeable for receipt of a sample of compacted asphalt mix therein, with the chamber sealable when closed;
   (b) a bleed valve to remove air from the chamber;

(c) a water source in fluid communication with the chamber to fill the chamber with water;

(d) an expandable flexible member positioned inside the chamber to cyclically apply pressure to the chamber, wherein when the expandable flexible member is expanded it forces water in the chamber to apply pressure to pores in the sample of compacted asphalt mix contained in the chamber.

2. An apparatus according to claim 1 further comprising a cone shaped lid used to seal the chamber, wherein said bleed valve is positioned at an apex of the cone shaped lid.

3. An apparatus according to claim 1 further comprising a heater for heating water introduced to the chamber.

4. A method to treat an asphalt sample for detection of susceptibility to moisture damage for asphalt mixes comprising:

(a) placing a sample of asphalt mix in a test chamber;
(b) adding water to the chamber containing the sample of asphalt mix therein;
(c) placing a lid on the chamber to close the chamber;
(d) decreasing the volume inside the closed chamber by expanding an expandable membrane in the chamber thereby pressurizing water in the chamber;
(e) bleeding air from the closed chamber;
(f) adding water to the closed chamber to replace the air bled from the chamber;
(g) pressurizing the closed chamber after air is bled from the chamber whereby pressure is applied to pores in the sample of asphalt mix in the chamber inducing physical changes in the sample.

5. A method according to claim 4 wherein the lid comprises a cone shaped lid with a bleed valve at an apex of the cone shaped lid whereby the bleed valve is used to bleed air from the chamber during expansion of the expandable membrane.

6. A method according to claim 5 further comprising heating water introduced to the chamber.

7. A method to treat an asphalt sample for determination of susceptibility of asphalt samples to moisture damage comprising:

(a) introducing an asphalt sample of a first known density to a chamber at least partially filled with water;
(b) placing a lid on the chamber to close the chamber;
(c) increasing pressure inside the closed chamber while bleeding air from the chamber;
(d) adding water to the closed chamber such that the chamber is substantially full of water;
(e) increasing and decreasing pressure in the closed chamber a predetermined number of cycles;
(f) removing the asphalt sample from the chamber and measuring a second density after said predetermined number of cycles and comparing the second density to the first known density of the asphalt sample.

8. A method according to claim 7 wherein the lid comprises a cone shaped lid.

9. A method according to claim 8 wherein the cone shaped lid includes a bleed valve at an apex thereof, and wherein bleeding air from the chamber comprises directing air toward the bleed valve with the cone shaped lid.

10. A method according to claim 9 further comprising heating water introduced into the chamber.

11. A method according to claim 7 further comprising cyclically inflating and deflating an inflatable flexible member to carry out the step of increasing and decreasing pressure in the closed chamber a predetermined number of cycles.

12. A method according to claim 11 wherein the inflatable flexible member is a rubber bladder.

13. A method according to claim 11 wherein the chamber has flexible rubber on at least one surface that defines the flexible member.

14. A method for determination of susceptibility of a compacted asphalt sample to moisture damage by measuring density before and after treatment with pressurized water, without mechanical pressure applied to said compacted asphalt sample, comprising:

(a) measuring a first density of a compacted asphalt sample;
(b) placing the compacted asphalt sample in a chamber;
(c) adding water to the chamber containing the compacted asphalt sample;
(d) sealably closing the chamber;
(e) cyclically applying pressure to the closed chamber by intermittently expanding an expandable flexible member in the chamber, wherein when the expandable member is expanded it forces the water in the chamber to apply pressure to pores in the compacted asphalt sample; then
(f) measuring a second density of the compacted asphalt sample;
(g) comparing the second density to the first density; and
(h) predicting the susceptibility of the compacted asphalt sample to moisture damage based on a difference in the first and second densities.

15. A method according to claim 14, the method further comprising the following steps carried out prior to the step of measuring a second density:

removing air from the closed chamber; and
adding additional water to the chamber to replace the air removed from the closed chamber.

16. A method according to claim 15 wherein:

sealably closing the chamber comprises placing a cone-shaped lid on the chamber; and
removing air from the closed chamber comprises directing air with the cone-shaped lid to a bleed valve on the cone-shaped lid.

17. A method according to claim 15 further comprising heating water introduced to the chamber.

18. A method according to claim 14 further comprising opening the chamber and removing the compacted asphalt sample from the open chamber after cyclically applying pressure to the closed chamber and before measuring the second density of the compacted asphalt sample.

* * * * *